United States Patent [19]

Litzie et al.

[11] Patent Number: 4,804,365
[45] Date of Patent: Feb. 14, 1989

[54] VASCULAR CANNULAE FOR TRANSFEMORAL CARDIOPULMONARY BYPASS AND METHOD OF USE

[75] Inventors: Ken Litzie, Irvine, Calif.; Craig P. Roberts, Dallas, Tex.

[73] Assignee: C. R. Bard, Murray Hill, N.J.

[21] Appl. No.: 14,926

[22] Filed: Feb. 13, 1987

[51] Int. Cl.⁴ .......................... A61M 5/00; A61M 1/03
[52] U.S. Cl. .......................................... 604/4; 604/53; 604/170; 604/280
[58] Field of Search ................ 604/4, 43, 44, 51–53, 604/93, 158–170, 178, 264, 280–284

[56] References Cited

U.S. PATENT DOCUMENTS

| | | | |
|---|---|---|---|
| 3,565,074 | 2/1971 | Foti | 604/164 |
| 3,788,328 | 1/1974 | Alley et al. | 604/178 |
| 4,531,935 | 7/1985 | Berryessa | 604/164 X |
| 4,650,472 | 3/1987 | Bates | 604/165 X |
| 4,661,094 | 4/1987 | Simpson | 604/164 X |
| 4,670,008 | 6/1987 | Albertini | 604/165 |
| 4,701,160 | 10/1987 | Lindsay et al. | 604/53 |

Primary Examiner—Dalton L. Truluck
Attorney, Agent, or Firm—Spensley Horn Jubas & Lulbitz

[57] ABSTRACT

A cannula assembly suitable for rapid, closed-chest cannulation of the cardiopulmonary system to an extracorporeal bypass machine through punctures in the femoral veins and arteries is disclosed. The assembly comprises a conduit made of a smooth, flexible, thin-walled material and capable of longitudinal insertion through these vessels by use of an associated "introducer" and conventional guide wire. The conduit has adequate hemodynamic flow capacity and sufficient unsupported hoop strength to resist collapse from suctional and vasoconstrictive forces during use.

12 Claims, 3 Drawing Sheets

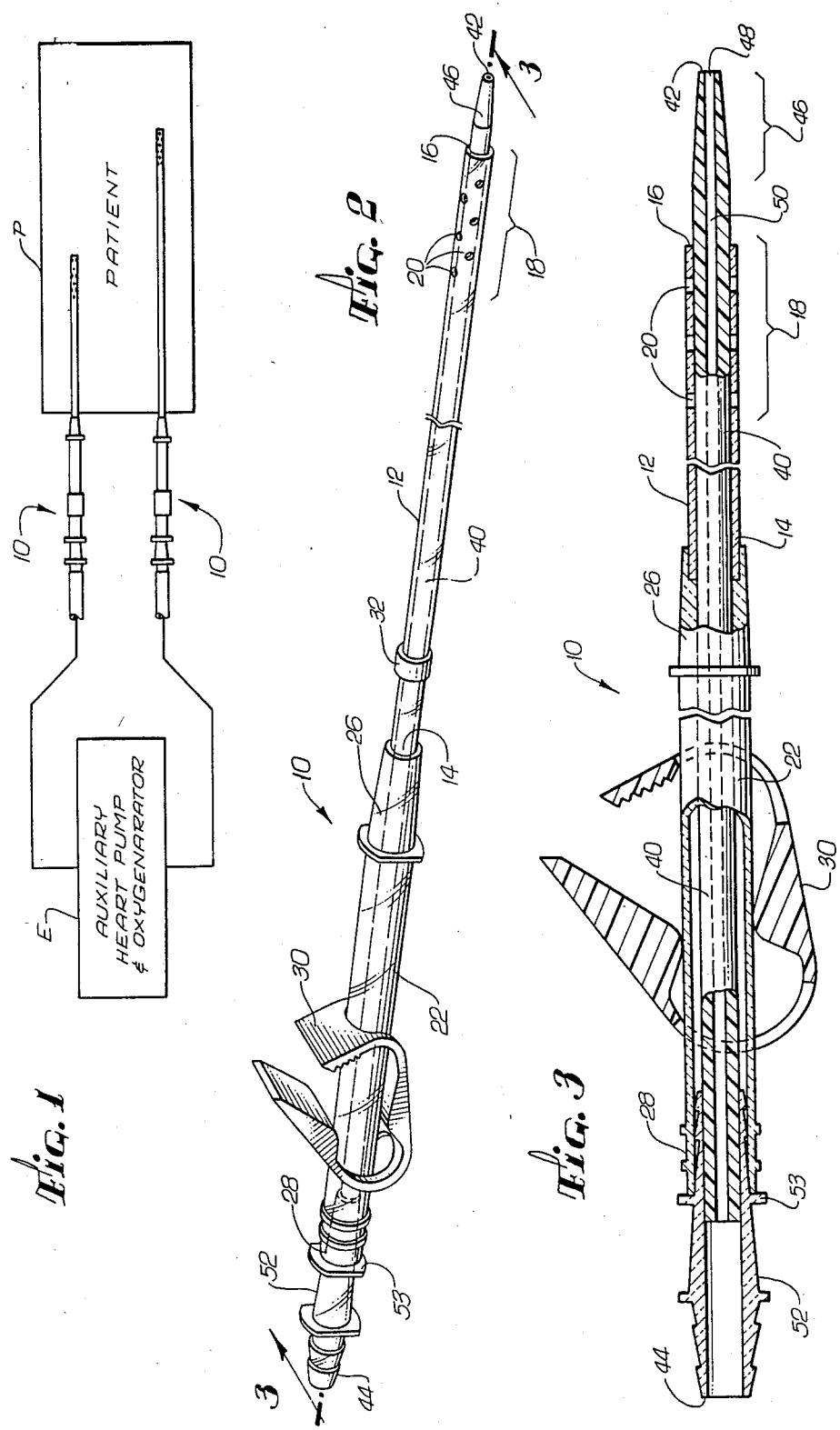

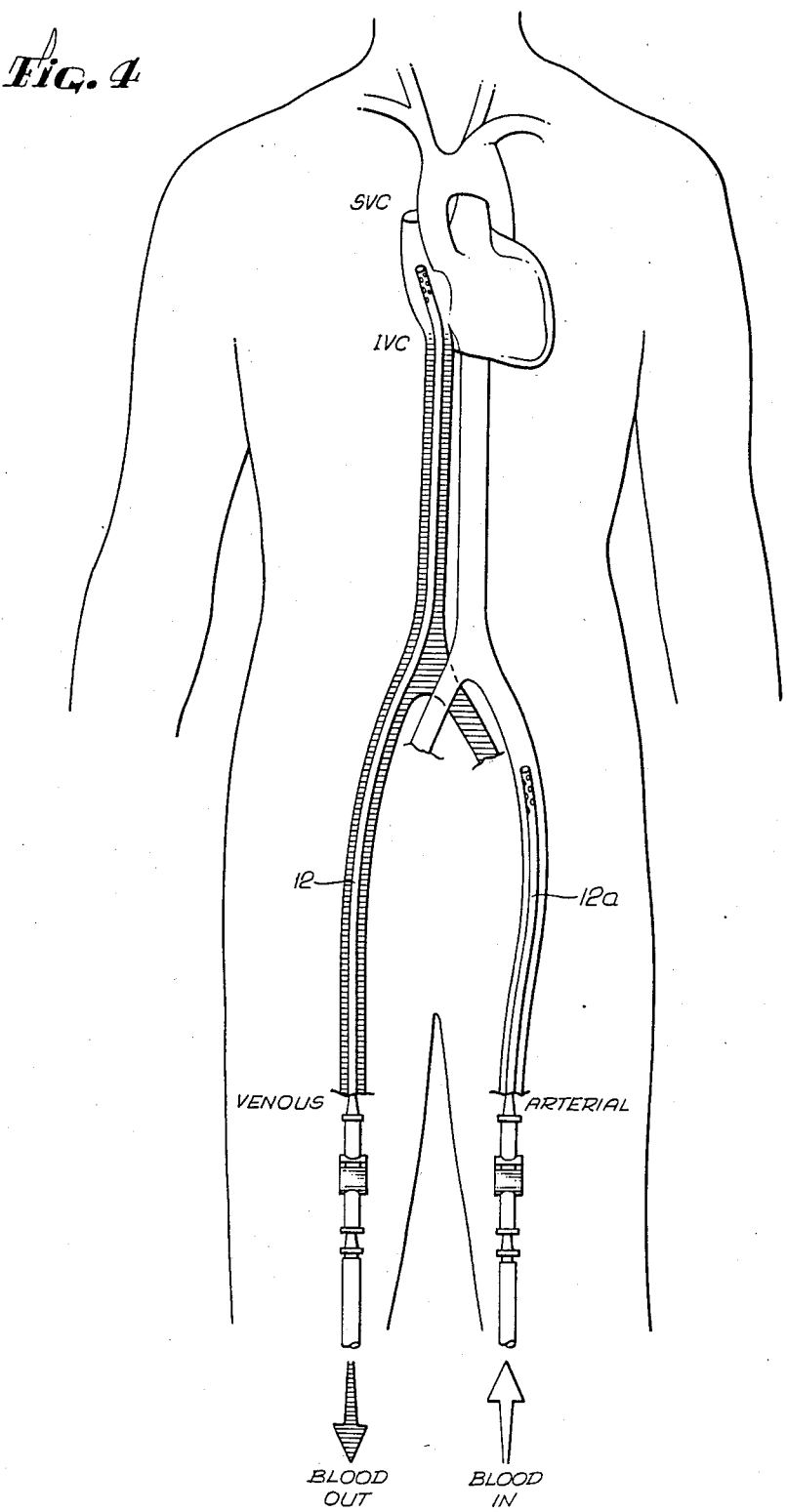

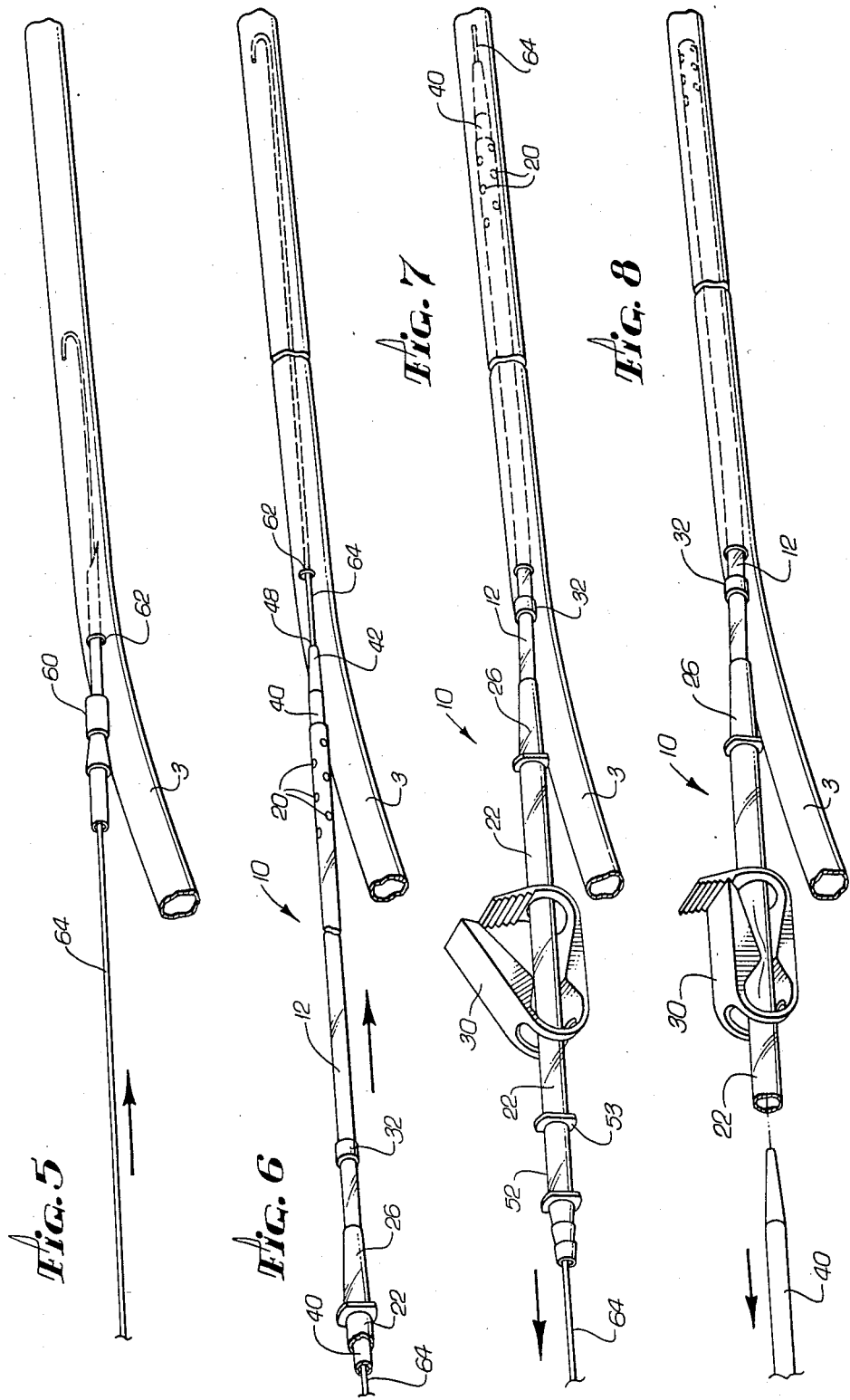

VASCULAR CANNULAE FOR TRANSFEMORAL CARDIOPULMONARY BYPASS AND METHOD OF USE

BACKGROUND OF THE INVENTION

1. Field of the Invention

This invention pertains to medical devices in general, and in particular, to a device for rapid, closed-chest cardiopulmonary cannulation through punctures in the femoral veins and arteries.

2. Description of Related Art

Life-threatening medical emergencies frequently encountered in typical hospital emergency rooms include myocardial infarction, cardiogenic shock, congestive heart failure, cardiac arrest, pulmonary embolus, pulmonary edema, profound accidental hypothermia, smoke inhalation, drowning and drug overdose. In any one of the foregoing situations, fast, competent cardiopulmonary bypass and support of the patient can often spell the difference between life and death.

In U.S. Pat. No. 4,540,399 to Litzie et al, a simplified, closed, extracorporeal heart-lung bypass system is described suitable for use in emergency situations.

Central to the utilization of such a system is the ability quickly to establish the bypass circuit between the patient and the machine, which in turn, requires a rapid access to venous and arterial blood. This can be achieved without opening the patient's chest by cannulation of the patient's cardiopulmonary system through the femoral veins and arteries, respectively, through incisions in the patient's upper thighs, provided suitable cannulae are at hand.

Use of cannulae as a means of draining or perfusing a cavity within the body is well known.

Amrine, in U.S. Pat. No. 4,129,129, discloses a venous return catheter, including an obturator used to control the flow of blood therethrough adapted to interconnect a patient's heart to a life support machine during open heart surgery, as well as the openchest surgical technique utilized for its placement.

In U.S. Pat. No. 4,033,331, Guss et al describe a cardiac catheter having a preformed distal end and a pair of parallel lumen. In one of the lumen a contour wire used to straighten or contour the catheter during or after insertion so that the outlet of the other lumen may be properly disposed to, e.g., inject an angiographic dye. Also discussed are a number of related devices and their method of use, all of which entail a time-consuming "cut down" procedure in which the vein or artery used to access the target region, including the femoral artery, is surgically prepared to receive the device.

Although these and other similar prior devices all represent contributions to the art, none are suitable for rapid cardiopulmonary bypass through the femoral veins or arteries for at least the following reasons: Those which are easily introduced through, e.g., a puncture created by a hypodermic needle, are too small to pass an adequate blood flow for successful bypass. Thus, they are suitable only for sampling or dye injection. Those having sufficient luminal area to transport an adequate blood flow are either so thin-walled as to rely entirely on the venous side to avoid kinking or collapse, as would be occasioned by the suctional forces associated with a positive extraction pump, or are so thick-walled as to result in a conduit that is both stiff and large in overall diameter. Such a conduit, if it can be inserted at all into a body vessel, requires a substantially long incision in the intended vessel for insertion, with a concomitant consumption of valuable time in surgical preparation and execution.

It is therefore an object of the present invention to provide a vascular cannula which is suitable for rapid, closed-chest, cardiopulmonary bypass through the femoral veins and arteries, and which is sufficiently smooth, flexible, thin-walled and narrow as to permit its rapid insertion through punctures created in those vessels by a hypodermic needle.

Yet another object of the present invention is to provide a cannula which posesses both sufficient luminal area to provide adequate hemodynamic flow of at least 2.0 liters/minute per square meter of body surface area during bypass, and an unsupported hoop strength sufficient to resist collapse from typical suctional and vasoconstrictive forces.

It is another object of the present invention to provide an associated, disposable means for introducing such a cannula which, when used in conjunction with a guide wire, is capable of inserting and guiding the cannula through the puncture and longitudinally through the vessel, for locating the distal end of the cannula within a predetermined venous or arterial region, and for supporting and obturating the cannular during insertion thereof.

It is yet another object of the present invention to provide a combination of the foregoing elements in a device which can be fabricated inexpensively and supplied to hospitals complete in a prepackaged, sterile unit ready for use.

It is still another object of the present invention to provide a method for using such a device in a cardiopulmonary bypass procedure.

SUMMARY OF THE INVENTION

These objects, and others, are achieved by the provision of the vascular cannula and introducer assembly of the present invention. The cannula comprises a smooth, elongated, flexible, open-ended, thin-walled, annular conduit. The conduit has proximal and distal ends, and a perforated portion adjacent the distal end. The conduit has an outside diameter which is sufficiently small as to permit the same to be readily inserted axially through a body vessel, but an inside diameter sufficiently large so as to permit adequate blood flow.

In one embodiment, the conduit has a length sufficient to permit it to extend at least from a first region adjacent the femoral artery in a patient's upper thigh to a second region in the common femoral or iliac artery. In a second embodiment, the conduit has a length sufficient to permit it to extend from the femoral vein in a patient's upper thigh to a second region near the junction of the superior vena cava and the right atrium of the heart. For any embodiment, the conduit also has means at the proximal end for connecting the cannula to an extracorporeal bypass machine.

The introducer comprises a smooth, elongated, flexible, annular trocar extending concentrically through the conduit. The trocar has an outer diameter sized to provide smooth, coaxial sliding within the conduit, while substantially obturating the conduit coextensively with the amount of trocar extending therethrough. The introducer has proximal and distal ends, and a tapered portion located adjacent the distal end tapering toward a point for vessel dilation. The distal end has an aperture extending longitudinally therethrough sized to receive a guide wire. The proximal end has means for stopping further longitudinal advancement of the trocar through the conduit when the tapered portion is in a desired position.

A procedure for using the assembly comprises the step of incising the skin to expose the femoral vessels and introducing a guidewire through the affected vein or artery by means of a hypodermic needle. The needle is then removed and the proximal end of the guidewire is inserted through the lumen of the introducer. Using the guidewire as a guide, the introducer and cannula combination are passed coaxially over the wire, through the puncture and advanced longitudinally through the vein or artery to a distance sufficient to permit the distal portion of the cannular to access the venous or arterial region desired. The guidewire and introducer are then simultaneously withdrawn from the cannula, and the cannula is clamped off prior to connecting its proximal end with the bypass machine.

A better understanding of the invention, its uses and its other objects and advantages, may be obtained from a consideration of the following detailed description of the preferred embodiments, particularly when read in conjunction with the appended drawings, a brief description of which now follows.

BRIEF DESCRIPTION OF THE DRAWINGS

FIG. 1 is a schematic illustration showing a venous and an arterial cannula interconnecting a patient to a cardiopulmonary bypass machine;

FIG. 2 is a perspective view of the cannula and introducer assembly of the present invention;

FIG. 3 is a sectional view of the assembly as revealed by section 3—3 taken in FIG. 2;

FIG. 4 is an anatomical illustration showing the cannulae of the present invention in place after insertion through punctures in the femoral veins and arteries of a patient;

FIG. 5 is a cutaway section of a femoral vein or artery showing the insertion of a guidewire through a puncture created by a hypodermic needle;

FIG. 6 shows the cannula installed over the guide wire and preceding insertion through the puncture into the femoral vessel;

FIG. 7 illustrates the cannula and introducer assembly after insertion through the femoral vessel;

FIG. 8 shows the cannula in place after withdrawal of the introducer and guidewire.

DETAILED DESCRIPTION OF THE PREFERRED EMBODIMENT

As broadly illustrated in FIG. 1, the vascular cannula assembly 10 of the present invention has been connected to a patient (P) and to an auxiliary heart pump and oxygenator equipment (E). By the use of assembly 10, the interconnection between patient (P) and equipment (E) can be quickly achieved. Greater detail of the assembly 10 and its method of use is set forth below.

An exemplary first preferred embodiment of a vascular cannula and introducer assembly 10 is illustrated generally in FIGS. 2 and 3. The assembly 10 comprises a smooth, elongated, flexible, open-ended, thin-walled tubular conduit 12 having a proximal end 14 and distal end 16. A portion 18 adjacent distal end 16 contains a plurality of radially-directed perforations 20 which extend through conduit 12.

An optically-clear tubular connector portion 22 is joined to the conduit 12 adjacent end 14. In the exemplary embodiment illustrated, the optically-clear connector portion 22 comprises a 4 inch length of silicon tubing joined to the proximal end 14 of conduit 12 by means of a plastic reducer 26. The proximal end 14 of conduit 12 is bonded within reducer 26 by means of an adhesive, although other conventional joining means are within the scope of this invention.

A conventional ribbed tapered portion 28 is formed on the proximal end of connector 22. Portion 28 provides a means for flow connecting the conduit 12 to an extracorporeal cardiopulmonary bypass system.

Since reducer 26 and connector 22 are also preferably made 4 of an optically-clear material, connector portion 22 facilitates the determination of when arterial or venous blood is present within the cannula at a region exterior of its point of insertion into the affected vessel, as well as the presence of any air bubbles in the blood.

It is preferable that means for clamping the cannula so as to prevent fluid flow be provided. This is necessary to prevent backflow during connection of the conduit 12 with a bypass machine or similar equipment. This feature may be effectively provided by the inclusion of a conventional Robert's clamp 30 captivated about tubular connector 22 in a conventional manner, to permit rapid, one-handed clamping and unclamping of the conduit 12.

The cannula assembly 10 also preferably includes adjustable marker means for marking off a predetermined length of conduit 12. This helps enable a practitioner to gauge the approximate length of the conduit to be inserted during cannulation in order to access a desired target region. In the embodiment illustrated, this marker means comprises a ring 32 which is slideably disposed about the outer circumference of conduit 12 adjacent end 14 with a fit sufficiently tight to cause ring 32 to remain in the position to which it is originally adjusted by the practitioner.

In addition to the conduit 12, the assembly 10 also includes an introducer 40 which incorporates means for inserting, supporting and guiding conduit 12 through a puncture created in the affected vessel, for advancing it through the vessel and for locating distal end 16 within the desired target region. In the case of a venous cannula, this target region is located, as discussed below, at the juncture of the superior and inferior vena cavas within the right atrium. In the case of an arterial cannula, the target region lies generally within the femoral or common iliac artery about 4"-6" from the entry point in the femoral artery.

In the exemplary preferred embodiment illustrated in FIG. 2, introducer 40 comprises a smooth, elongated, flexible, hollow, trocar-like tube having a cross-section configured to provide smooth, coaxial sliding within conduit 12, while yet substantially obturating conduit 12. Introducer 40 has distal and proximal ends 42 and 44, and a tapered portion 46 adjacent distal end 42 tapered portion 46 is used to dilate the punctured and affected vessel during insertion and advancement of assembly 10.

Unlike a conventional trocar, which is rigid and is used forcefully to penetrate the wall of a cavity for, e.g., drainage thereof, introducer 40 is flexible and functions differently. Introducer 40 includes a small aperture 48 extending coaxially through its distal end which opens into a long bore 50 extending coaxially throughout the length of the introducer 40. Aperture 48 is sized to accommodate in a sliding relationship the outer diameter of a conventional guidewire 64 (see FIGS. 5-8). As discussed below, wire 64 cooperates with tapered portion 46 to permit the distal end 16 of conduit 12 to be inserted through a puncture site in the affected vessel, and to be advanced longitudinally therethrough without tearing the vessel.

In the preferred embodiment illustrated, introducer 40 includes a conventional tubing adapter 52, the distal end of which includes a shoulder 53. Shoulder 53 is designed to stop further coaxial advancement of introducer 40 through conduit 12 when the introducer's tapered portion 46 is extended beyond the distal end 16 of conduit 12. In this position, conduit 12 is both completely obturated and supported radially along its length by the introducer 40. Further, relatively sharply-tapered portion 46 of introducer 40 encourages dilation of the blood vessels and thus ease of insertion of assembly 10.

Connector 52 additionally provides means for grapsing and withdrawing introducer 40 from the proximal end 14 of conduit 12 after the cannula assembly 10 has been placed appropriately.

Introducer 40 may be fabricated using a number of methods and materials, so long as it retains both sufficient strength and flexibility to permit its use as an aid in introducing the conduit 12 into place. Additionally, its cross-sectional area must be controlled relative to the luminal diameter of conduit 12 to permit a relatively close fit therebetween. As an example, introducer 40 can be molded from polyurethane, which may be colored appropriately to permit practitioners to easily relate them to the particular cannulae with which they are associated, i.e., blue for venous cannula and red for arterial cannula.

For reasons of hemodynamic flow resistance, it is desirable tha the lumen of conduit 12 be large and smooth in order to accommodate adequate hemodynamic flow characteristics between the patient and the bypass machine while minimizing the hemolytic effect of the procedure as much as possible. Accordingly, "adequate" in this context and as applied to the minimum-acceptable lumen diameter of the instant cannula, means that diameter which, when taken in conjunction with the length of the cannula necessary to access the particular target region desired, along with the frictional coefficients associated with the internal surface of the cannula's walls, results in a flow of blood sufficient to result in a flow capacity of 2.0-3.0 liters/min/m$^2$ body area (cardiac index) without undue hemolytic effect being introduced by virtue of the presence of the cannula itself. Preferably, the flow capacity is about 2.2 liters/min/m$^2$ of body surface area.

In the exemplary preferred assembly illustrated in FIG. 2, the necessity for a time-consuming surgical cutdown procedure is obviated by reducing the outer diameter of conduit 12 and by making it sufficiently flexible to permit its insertion into the affected vessel through a puncture site created by a hypodermic needle, in the procedure described hereinafter. It has been learned that a cannula for an average adult patient in accordance with the present invention may have an outer diameter not in excess of about 21 Fr. in order to permit its insertion through a puncture in the wall of the affected vessel without tearing the vessel, and without the necessity of creating an elongated incision in the wall of the vessel. This maximum diameter may be decreased slightly to a minimum of about 19 Fr. and still meet the flow requirements of the cannula. Accordingly, conduit 12 of the present invention intended for use with an average adult (human) patient includes an outer diameter in the preferred range of between about 6.32 and 6.98 millimeters (19-21 Fr.).

Analogous to the luminal diameter constraints discussed above, larger patients can tolerate cannulae having outer diameters larger than the average range, whereas smaller patients, e.g., children, will require cannula having smaller outer diameters.

Skilled practitioners will recognize that these two constraints will by necessity result in a cannula that is relatively thin-walled. However, another important consideration that the cannular not collapse when subjected to the relatively strong radial forces exerted by the vessel. This is particularly true on the venous side where there are suctional forces generated by the emergency bypass pump when the cannula is in place.

It has been discovered that a relatively thinwalled and flexible cannula can be fabricated which possesses sufficient hoop strength to resist collapse from vasoconstrictive and suctional forces, while accommodating the constraints of the preferred outer diameter and inner diameter ranges discussed above. In the preferred embodiment, this is achieved by extruding conduit 12 from a relatively strong, yet flexible, plastic material, such as one of the fluorocarbon plastics (e.g., "PTFE"). Other plastic materials may also be used.

Accordingly, an exemplary preferred embodiment of the present invention includes a conduit 12 extruded in an annular or circular cross-section from PTFE, which has an outer diameter of about 19-21 Fr. and a wall thickness of from about 0.35-0.40 mm.

As noted above, located adjacent distal end 16 is a perforated portion 18 containing a plurality of radially-directed apertures 20. The purpose of apertures 20 is two-fold, namely, to minimize orifice flow resistance through conduit 12 and to permit adequate perfusion or aspiration to be achieved within the particular arterial or venous target region, respectively, to which the cannula is directed. Sufficient aperatures are present such that even in the event open distal end 16 of conduit 12 should become occluded during bypass, adequate flow through conduit 12 is maintained.

Depending upon whether the cannula is intended for use as an arterial cannula or a venous cannula, conduit 12 will have a length sufficient to permit its extension through a puncture in the femoral vein or artery and through the affected vessel to either a second region within the femoral or common iliac artery, or to a third region located at the intersection of the patient's superior and inferior vena cavas and right atrium, respectively. (See Fig. 4.) Accordingly, a preferred embodiment of a venous cannula includes a conduit 12 having a length of from about 45-75 cm, whereas a preferred arterial cannula includes a conduit 12a having a length of from about 10-45 cm.

An important object of the present invention is the provision of an assembly which permits rapid, closed-chest cannulation of the patient's cardiopulmonary system to a bypass machine through a small puncture in a femoral vein or artery. Such a procedure obviates the necessity for an extensive, time-consuming cut-down procedure of the affected vessels, as required for conventional cannulae. Accordingly, a method for using the above-described assembly 10 to achieve this is now described.

After the patient's condition has been diagnosed as appropriate for cardiopulmonary bypass, it is essential that the procedure be instituted as rapidly as possible to permit rapid, stabilized support to be achieved.

The method of the present invention adopts a variation on known techniques for catheterization of a particular circulatory region using devices typically much smaller than the present invention for, e.g., angiography, ventricularography, etc.

The first step of the present method is to estimate the length of conduit 12 which is to be advanced in order to access the desired target region.

In the case of a venous conduit 12 (see FIGS. 2-4), this is accomplished by placing distal end 16 of the cannula-and-introducer assembly 10 on the patient's chest at a position approximating the right atrium of the patient's heart and extending the proximal end 14 of assembly 10 along the patient's chest and torso to the region at the patient's upper thigh. Marker 32 is then positioned along conduit 12 until it is approximately at the location of the intended point of penetration. This permits a rapid approximation of the length of the conduit which will be into vein 3. (See FIG. 5-8).

At the same time marker 32 is positioned, the point of entry on the patient's thigh is also marked and a slight nick or incision is created at the point subcutaneously by using, e.g., a Kelly, or the closed point of a pair of Metzenbaum clamps until the vessel is visualized. This step departs from prior art techniques because, in the subsequent step of inserting the point of a hypodermic needle, it is preferable that the tip not pierce the posterior wall of the vessel.

Thus, the next step of the preferred method comprises introducing the point of a hypodermic needle 60 through the exposed, anterior wall of the vessel only, and into vein 3 to create a small puncture site 62 therein. (See FIG. 5.) When the needle has been introduced into the vein, the distal end of a conventional guidewire 64 may be inserted through the needle's lumen and advanced relatively quickly to the target region.

When guidewire 64 is in place, hypodermic needle 60 is removed from the puncture 62 and slid off the proximal end of guidewire 64. The proximal end is then threaded coaxially through aperture 48 in distal end 42 of introducer 40 and extended through the lumen 50 of introducer 40. (See FIG. 6.)

Assembly 10 is then ready to be inserted. This is accomplished by simultaneously rotating or twisting the assembly's distal end while inserting it through the puncture 62 created by the needle. When the tip of the introducer's taper is past the puncture, the distal end of the assembly 10 is then oriented more coaxially with the femoral vein and, while continuing with the twisting or rotating movement of the device, the distal end is firmly advanced longitudinally through the vessel along wire 64 until marker 32 is immediately adjacent the patient's upper thigh at the puncture 62. (See FIG. 7.)

When the cannula assembly 10 is in place, guidewire 64 and introducer 40 may then be withdrawn simultaneously. Typically, a column of blood will then flow through conduit 12, the progression of which may be visually ascertained through the translucent connector portion 22. When introducer 40 has been withdrawn, clamp 30 may be engaged to clamp off the conduit 12 to prevent loss of any significant amount of blood and to prevent backflow into vein 3. (See FIG. 8.) Proximal end 14 of the cannula is then connected to an extracorporeal cardiopulmonary bypass machine (not shown) and the bypass circuit on the patient's venous side is complete. (See FIG. 4.)

Cannulation of the patient's arterial side is accomplished in substantially the same way as the aforedescribed procedure, except that a shorter, arterial conduit 12a is used and is advanced to a target region within the femoral artery or common illiac artery. (See FIG. 4.)

By now, skilled practitioners will recognize that a number of modifications of both the device and its method of use are possible in terms of materials and methods of manufacture and technique, and will depend upon the particular problems of the patient at hand. Accordingly, the embodiments illustrated and discussed herein should be taken as exemplary in nature, and the spirit and scope of the instant application should be limited only by the claims attended hereto.

What is claimed is:

1. A cardiopulmonary bypass system for rapid, closed-chest, cardiopulmonary cannulation during a cardiopulmonary bypass procedure, comprising:

a first smooth, elongated, flexible, open-ended, thinwalled conduit having proximal and distal ends, a perforated portion adjacent said distal end, and having an outer diameter sufficiently small to permit said conduit to be inserted through a puncture in a femoral vein and advanced through said vein, and an inner diameter selected such that the hemodynamic flow of blood through the first conduit during use is approximately 2.2 lit./min./m$^2$ of body surface area;

first flexible introducer means for inserting and guiding said first conduit through said puncture and coaxially through said vein, and for obturating said conduit during insertion thereof;

first connector means joined to said first conduit adjacent said proximal end for connecting said proximal end of said conduit to an extracorporeal cardiopulmonary bypass system;

a second smooth, elongated, flexible, open-ended, thinwalled conduit having proximal and distal ends, a perforated portion adjacent said distal end, and an outer diameter sufficiently small to permit said second conduit to be inserted through a puncture in a femoral artery and advanced through said artery, and an inner diameter selected such that the hemodynamic flow of blood through the second conduit during use is approximately 2.2 lit./min./m$^2$ of body surface area;

second flexible introducer means for inserting and guiding said second conduit through said puncture and coaxially through said artery, and for obturating said conduit during insertion thereof; and second connector means joined to said second conduit adjacent said proximal end for connecting said proximal end of said second conduit to an extracorporeal cardiopulmonary bypass system.

2. The sytem of claim 1, wherein said first and second conduits are made of polytetrafloroethylene.

3. The system of claim 1, wherein said first and second conduits each have an outside diameter of from about 6.3 to 7.0 mm and a wall thickness of from about 0.35 to 0.40 mm.

4. The system of claim 1 wherein said first and second conduits have a hoop strength sufficient to permit a hemodynamic flow of approximately 2.2 lit./min/m$^2$ of body surface area through each of said conduits during use without collapse.

5. The system of claim 1, wherein said first conduit is of a length sufficient to permit said first conduit to extend from said puncture site in the femoral vein to the junction of the superior vena cava and the right atrium.

6. The system of claim 1, wherein said second conduit is of a length suffcent to permit said second conduit to extend from said puncture site in the femoral artery to a site in the proximal femoral or iliac artery.

7. The system of claim 1, further including means for clamping said first and second conduits.

8. The system of claim 1, further comprising:
marker means disposed on each of said first and second conduits and movable longitudinally for marking the length of insertion of each of conduits through said vessels.

9. The system of claim 1 wherein said first and second connector means are made of a clear material.

10. The system of claim 1 further including:
guidewire means for introducing said first and second conduits and said first and second introducer means into an associated vein or artery.

11. The assembly of claim 10, wherein said first conduit has an outside diameter of from about 6.3 to 7.0 mm, and a wall thickness from about 0.35 to 0.40 mm.

12. A method for rapid, closed-chest, vascular cannulation of a patient's cardiopulmonary system, comprising the steps of:
advancing a guide wire through a puncture site in a patient's upper femoral vein or artery and into a predetermined region of said patient;
sliding an in-line conduit and flexible introducer assembly coaxially over said guide wire, through said puncture site and said vein or artery to said predetermined location in said patient, said conduit having a wall thickness of from about 0.35 to 0.40 mm;
removing said guide wire and said introducer, thereby placing said conduit at said predetermined location; and
flowing a body fluid through the conduit at a rate of approximately 2.0 to 2.2 lit./min/m$^2$ of said patient's body surface area.

* * * * *